73-637
9/15/81    XR    4,289,033    SR

United States Patent [19]
Prause et al.

[11]    4,289,033
[45]    Sep. 15, 1981

[54] ULTRASONIC TEST APPARATUS FOR TUBES AND RODS

[75] Inventors: Reinhard Prause, St. Augustin; Udo Schlengermann, Erftstadt, both of Fed. Rep. of Germany

[73] Assignee: Krautkramer-Branson, Inc., Stratford, Conn.

[21] Appl. No.: 122,027

[22] Filed: Feb. 19, 1980

[30] Foreign Application Priority Data

May 18, 1979 [DE] Fed. Rep. of Germany ....... 2820142

[51] Int. Cl.³ ............................................. G01N 29/04
[52] U.S. Cl. ........................................ 73/622; 73/637
[58] Field of Search ................. 73/622, 637, 638, 640

[56] References Cited

U.S. PATENT DOCUMENTS

| | | | |
|---|---|---|---|
| 3,552,190 | 1/1971 | Lefebvre | 73/622 |
| 3,924,453 | 12/1975 | Clark et al. | 73/622 |
| 3,981,184 | 9/1976 | Matay | 73/622 |
| 4,195,530 | 4/1980 | Ross et al. | 73/638 |

*Primary Examiner*—Anthony V. Ciarlante
*Attorney, Agent, or Firm*—Ervin B. Steinberg; Philip J. Feig

[57] ABSTRACT

An ultrasonic test apparatus for testing tubes or rods by rotating transducers to provide a helical scan, the test transducer, or each of a plurality of transducers, is mounted for adjustable motion along an axis which is inclined by an angle $\omega$ with respect to a perpendicular axis intersecting the workpiece surface. The angle $\omega$ is selected to provide a desired incident angle $\alpha$ of the ultrasonic energy upon the workpiece surface, whereby to cause a refracted angle $\beta$ of the ultrasonic energy. Within the range of measuring accuracy for small angles it can be assumed that angle $\omega$ approximates angle $\alpha$.

5 Claims, 4 Drawing Figures

ULTRASONIC TEST APPARATUS FOR TUBES AND RODS

SUMMARY OF THE INVENTION

This invention concerns an ultrasonic test apparatus for discerning defects in tubes and rods wherein the ultrasonic energy is beamed obliquely into the workpiece and wherein the test probes are mounted adjustably for motion along straight axes which are inclined relative to respective axes intersecting the workpiece surface at a right angle.

When testing workpieces which must be tested by transmitting ultrasonic energy obliquely toward the workpiece surface, such as when testing tubes or rods, it is necessary to accurately maintain predetermined angles and distances between the respective test probe and the workpiece surface in order to assure reliable test results, see "Ultrasonic Inspection of Seamless Drill Casing and Linepipe", Materials Evaluation, vol. 36, September 1978, pp 57-68 and 71. These parameters, however, must be changed depending upon the diameter of the workpiece and the wall thickness of the tube. When a test apparatus includes a plurality of test probes (transducers) this requirement entails prolonged adjustments.

In the prior art, see Krautkramer, "Ultrasonic Testing of Materials" (book), 2nd edition (1977), Springer Verlag, pages 447 to 457, an arrangement is shown wherein, in part, the adjustment of the angle is eliminated since adjustment is obtained by the tube curvature. This arrangement, however, is afflicted with shortcomings in that the water coupling path from the probe to the tube changes as a function of tube diameter. Adjustment means which permit the adjustment of both parameters, angle and distance, independently from one another require prolonged set up times and complicated mechanisms.

The present invention has as its principal object the provision of a test apparatus of the type stated heretofore which is characterized by a simple, yet accurate, adjustment of the transducer probe.

The instant invention is based upon the fact that the required positioning of the transducer probes as a function of tube diameter and wall thickness is achieved by mounting each transducer for positioning along a respective axis which is inclined by a predetermined angle relative to a normal axis intersecting the workpiece and which has a predetermined distance from the axis of the workpiece. Upon moving the transducer along such inclined axis, all of the required combinations of angles of incidence of the ultrasonic energy and distances required for testing different tubes and rods can be achieved solely by such translating motion. A change in adjustment necessitated, for instance, when testing a tube of a different diameter can be accomplished in a significantly simpler and more accurate manner than has been possible in the prior art devices.

Moreover, automation of the transducer adjustment is far simpler since only a linear motional adjustment is required. Due to the linear motion requirement a relatively simple central adjustment means can be utilized for simultaneously adjusting a plurality of transducers which are mechanically coupled to one another.

The details of the present invention and its inherent advantages will be more clearly apparent when reading the following description in conjunction with the accompanying drawings.

DETAILED DESCRIPTION OF THE INVENTION

Figure 1:
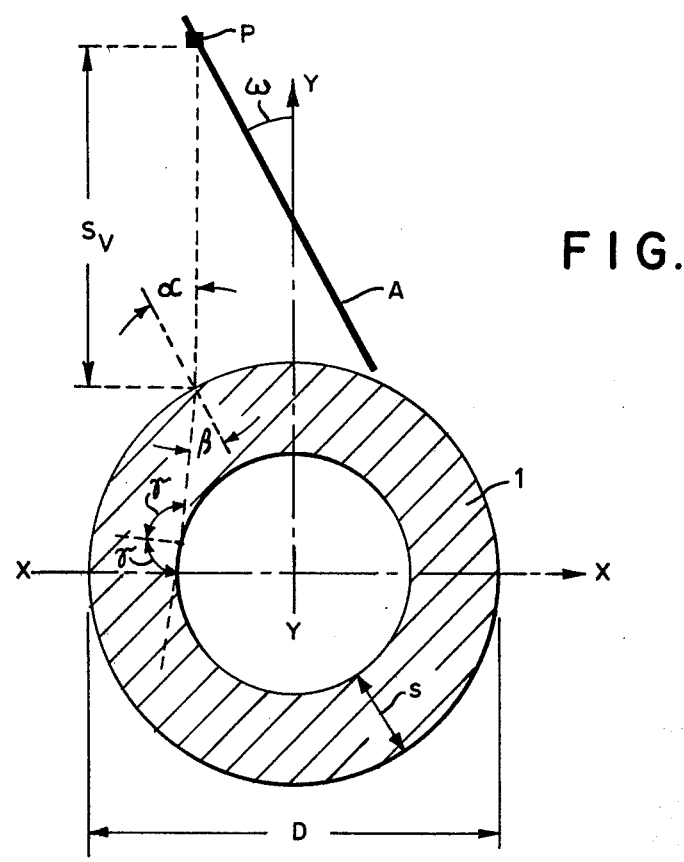
FIG. 1 is a schematic view of an arrangement for testing tubes.

With reference to the figures and FIG. 1 in particular, numeral 1 designates a tube having a diameter D and wall thickness s which is to be tested for defects. An ultrasonic transducer P, mounted for rotation about the tube 1, is adjustably positionable along an axis A. The ultrasonic waves after passing through the coupling path, for instance water, having a length $S_V$ are incident upon the tube 1 with an angle $\alpha$ and are propagated within the wall of the tube at a refracted angle $\beta$, also called at times angle of emergence. Only shear waves will be considered in the following description.

From the angle $\omega$, which is the angle between the inclined axis A and the perpendicular axis y, the angle of refraction $\beta$ can be determined for a predetermined maximum wall thickness diameter ratio s/D. The ratio s/D should always be smaller than 0.2 since otherwise longitudinal waves falsify the measurement.

It is assumed, for example, that a steel tube having a maximum wall thickness diameter ratio s/D=0.151 is to be tested. Then it follows from $\sin \beta = \sin \gamma (1 - 2s/D)$, see FIG. 1, when $\gamma_{max} = 90°$ for $\beta_{max} = 44°$. If angle $\beta = 40°$ is chosen in order to assure that reflection occurs at the inner wall, then an incident angle $\alpha = 18.5°$ is obtained from the ratio:

$$\sin \alpha / \sin \beta = c_1/c_2$$

wherein $c_1$ is the acoustic velocity of the coupling medium (water) and $c_2$ the acoustic velocity of the workpiece.

Since, moreover, geometric considerations show: $\tan \omega \simeq \sin \alpha$, it can be assumed within the range of measuring accuracy for small angles that: $\omega \simeq \alpha$.

Therefore, the inclined axis A in the present example should have an inclination of 18.5°. For a maximum wall thickness $s_{max} = 5$ mm a coupling path length of $S_V > 6$ mm is obtained. The transit time of the ultrasonic signal through the coupling path should be greater than the maximum expected transit time of the signal in the workpiece in order to avoid misleading test indications.

Figure 2:
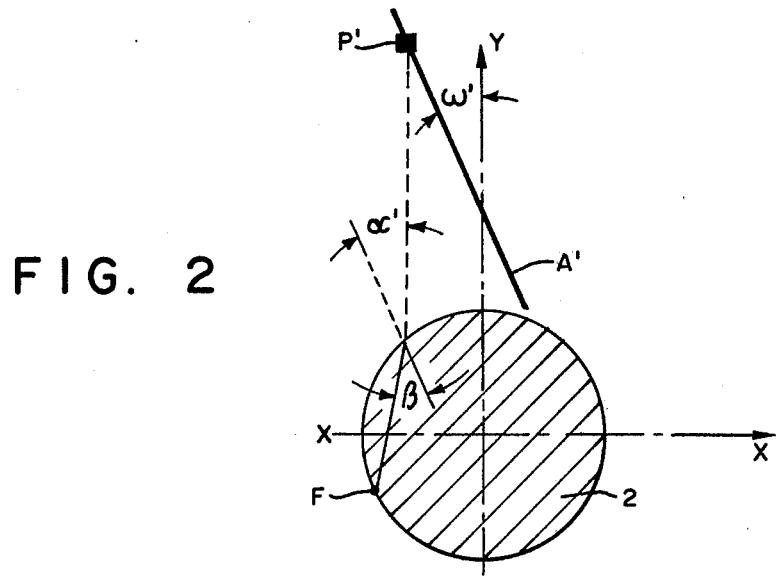
FIG. 2 is a schematic view of an arrangement for testing rods.

FIG. 2 shows the corresponding relations for rods 2. In principle, the same considerations apply as with tubes. However, given the fact that no reflection occurs at the inside wall, the selection of the angle of refraction $\beta$ and, hence, the inclination angle $\omega'$ of the axis A' is relatively non-critical. If neither longitudinal waves nor surface waves should form a part of the measurement, angle $\beta$ must be between 35° and 55°. Substantially all of the surface cracks F are detected as the result of the test transducers P' rotating about the workpiece.

Figure 3:
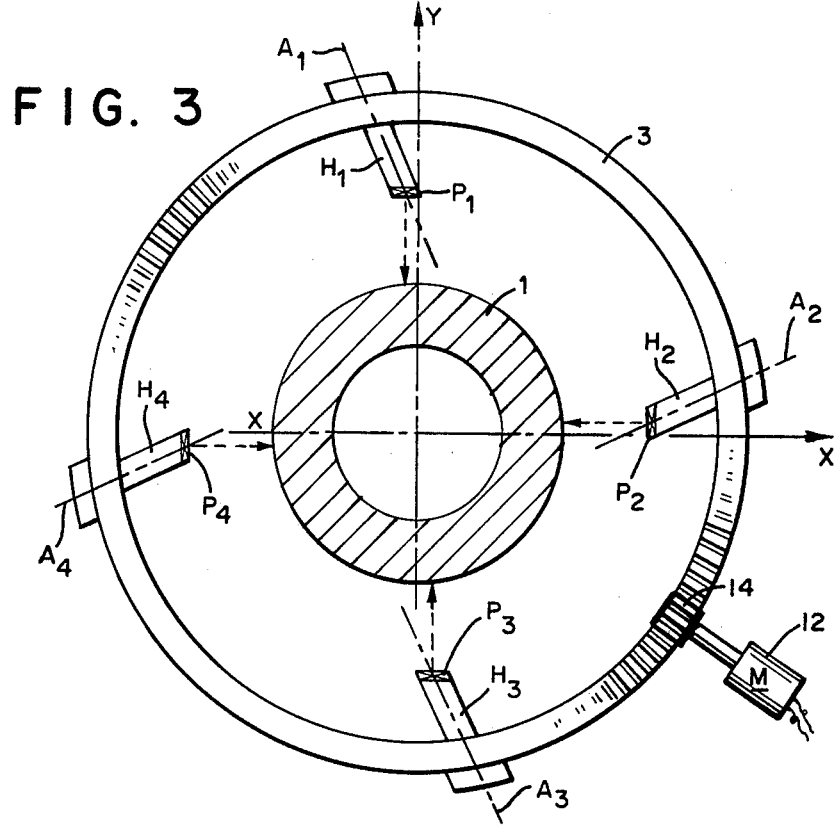
FIG. 3 is a schematic illustration showing the adjustment of a plurality of transducers by a central adjustment means.

FIG. 3 schematically illustrates a means for adjusting transducers $P_1$, $P_2$, $P_3$ and $P_4$ by a central control. The support means $H_1$, $H_2$, $H_3$ and $H_4$, each containing a respective test transducer, are moved along respective inclined axis $A_1$, $A_2$, $A_3$ or $A_4$ responsive to rotation of a ring gear 3 which is controlled by a servomotor 12 via a gear 14.

Figure 4:
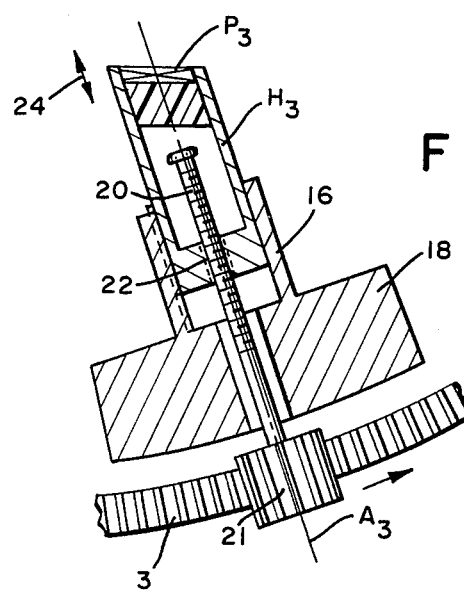
FIG. 4 is a detailed illustration showing the adjustment mechanism for a transducer.

FIG. 4 shows the motion of the transducer $P_3$ along axis $A_3$ in greater detail. The transducer probe $P_3$ is mounted in a support or mounting means $H_3$ which is retained for non-rotational axial motion in a sleeve 16 extending from a support frame 18. A threaded rod 20 engages the threaded portion 22 of the mounting means $H_3$ and at its outer end is provided with a gear 21 which meshes with the ring gear 3. Hence, motion of the ring gear as controlled by the servomotor 12 causes linear motion of the transducer $P_3$ along inclined axis $A_3$ as indicated by the double headed arrow 24. It will be apparent that the mechanism illustrated in this figure is duplicated for the other transducers.

This invention, of course, is not limited to the testing of longitudinal defects, but can be used also for detecting transverse defects present in tubes and rods using ultrasonic energy. In the latter case, the inclined axis lies in the y-z plane wherein the z-direction corresponds to the axis of the tube.

What is claimed is:

1. An ultrasonic test apparatus for testing tubes and rods in which ultrasonic energy after traversing a coupling medium obliquely enters the surface of the respective workpiece and is propagated therein comprising:
   transducer means disposed for transmitting ultrasonic energy toward the workpiece to be tested;
   mounting means for supporting said transducer means and causing said transducer means to be adjustably movable along an axis which is inclined by an angle $\omega$ relative to a perpendicular axis intersecting the surface of the workpiece;
   said angle $\omega$ when testng tubes substantially corresponding to the angle of incidence $\alpha$ of the ultrasonic energy upon the workpiece and which for a maximum predetermined wall thickness to diameter ratio of the tubes provides an angle of refraction $\beta$ of the ultrasonic energy, and when testing rods the angle $\alpha$ is selected to provide an angle of refraction $\beta$ of greater than 35°, and
   said transducer means being spaced from the workpiece surface for causing the transit time of the ultrasonic energy in the coupling medium to be longer than the maximum transit time of the ultrasonic energy in the workpiece.

2. An ultrasonic test apparatus for testing tubes and rods as set forth in claim 1, said angle $\beta$ being less than 55° when testing rods.

3. An ultrasonic test apparatus for testing tubes and rods as set forth in claim 1, said transducer means comprising a plurality of test transducers, each adjustably movable along a respective inclined axis, and a common control means coupled to said mounting means for adjustably moving said transducers simultaneously along their respective axes.

4. An ultrasonic test apparatus for testing tubes and rods as set forth in claim 3, said common control means and said mounting means being interconnected by gearing.

5. An ultrasonic test apparatus for testing tubes and rods as set forth in claim 3, said common control means including a ring gear.

* * * * *